United States Patent [19]

Maddoux

[11] 4,447,418

[45] May 8, 1984

[54] ANIMAL MEDICINE

[76] Inventor: Lilla A. Maddoux, 514 N. 5th, Sayre, Okla. 73662

[21] Appl. No.: 364,761

[22] Filed: Apr. 2, 1982

Related U.S. Application Data

[63] Continuation of Ser. No. 241,451, Mar. 6, 1981, abandoned.

[51] Int. Cl.³ .................... A61K 33/04; A61K 35/60
[52] U.S. Cl. .................................. 424/165; 424/95; 424/195; 424/164
[58] Field of Search .................. 424/196, 95, 303, 164, 424/165

[56] References Cited

U.S. PATENT DOCUMENTS

| | | | |
|---|---|---|---|
| 970,434 | 9/1910 | Dooley | 424/196 |
| 2,253,182 | 8/1941 | Klarmann | 424/196 |
| 2,361,756 | 10/1944 | Fiero | 424/303 |
| 2,761,805 | 9/1956 | Huidobro et al. | 424/196 |

OTHER PUBLICATIONS

Rossoff–Handbook of Veterinary Drugs (1974), Springer Pub. N.Y., pp. 222, 298, 398, 581 & 627.

*Primary Examiner*—Sam Rosen
*Attorney, Agent, or Firm*—Ely Silverman

[57] ABSTRACT

Manufacture and use of a therapeutic composition which provides for healing of open wounds on animals such as horses while avoiding the development of proud flesh and while acting as a fly repellent and avoiding and curing bacterial infection.

7 Claims, No Drawings

ANIMAL MEDICINE

This application is a continuation, of application Ser. No. 241,451, filed Mar. 6, 1981 now abandoned.

BACKGROUND OF THE INVENTION

1. The Field of the Invention

The field of art to which this invention pertains is veterinary medicine of the ointment type for topical application.

2. Description of the Prior Art

While the history of topically applied ointments for healing of external wounds has a history long in time and has also provided many compositions directed to the healing of animal wounds, where infection occurs healing usually is delayed and scar tissue develops. Also, scar tissue frequently develops whether or not there is infection because in the usual topically applied ointments healing occurs from the outside inward, with the result that scar tissue develops at the site of the wound. Such scar tissue, known as "proud flesh", is damaging to the value of show horses and race horses because such proud flesh substantially detracts from the appearance of the animal, which is of special importance in race horses and show horses, as well as resulting in tension and stiffness at such areas of proud flesh tissue.

By the use of the product of this process healing of wounds occurs from the inside outward and avoids the development of such proud flesh.

Examples of the prior art on this subject are compositions used for topical application are known as:

(a) Purple Lotion Spray comprising Crystal Violet, Carbolic Acid, Tannic Acid and Isopropyl Alcohol, and (b) Scarlet Oil comprising Oil Eucalyptus, Methyl Salicylate, Carbolic Acid, Biebuch Scarlet and Hydrocarbon Oil.

(c) U.S. Pat. No. 78,068 used one-half pint turpentine, one-half pint of fish oil and one ounce of oil of vitriol mixed in an iron vessel: such composition was used as a liniment, not as a healing ointment, and does not provide a stable solution that can be stored and sprayed.

SUMMARY OF THE INVENTION

Long chain polyunsaturated acid components of fish oil are partially cross linked with terpenes to provide a tissue penetrant solvent in which are successively dissolved oleic acid and kerosene to provide an adherent protecting oily liquid that is destructive to aerobic bacteria and promotes healing of equine wounds from the interior surface of such wounds outward to the surface of such wounds and avoids proud flesh production during healing.

DESCRIPTION OF THE PREFERRED EMBODIMENT

To one pint (16 fluid ounces or 473 ml) of fish oil of light orange color in a smooth surfaced ceramic vessel or PYREX at room temperature there is slowly added with continuous mixing a pint (16 fluid ounces) of spirit of turpentine. This operation forms a first orange-colored homogeneous liquor as a first combination composition. The fish oil is comprised of glycerides of olefinic polyunsaturated straight chain hydrocarbon acids of 20 to 24 carbons which have between 1 and 6 double bonds per chain. The fish oil also contains effective (e.g. 0.02%) amounts of vitamin E (alpha tocopherol) to serve as an anti-oxidant as well as having therapeutic value.

The spirit of turpentine consists essentially of a number of terpene hydrocarbons having the general formula of $C_{10}H_{16}$ primarily as $\alpha$ pinene, but also including $\beta$ pinene, camphene, $\Delta^3$ carene, dipentene, and terpinolene, all of which terpenes have a 6-member carbon ring and an olefine bond and all have boiling points in the range of 156 degrees C. to 180 degrees C. and a specific gravity in the range of 0.872 to 0.8415.

To this resulting combination composition formed of solutions of turpentine and fish oil in the vessel there is slowly added, with continuous stirring, one ounce of concentrated (96%) sulfuric acid (which has a specific gravity of 1.835 at 20 deg. C.) although 93% to 98% $H_2SO_4$ can be used. This addition forms a reaction liquor.

During this slow addition (over a period of 2 minutes) the texture and the color of the reaction liquor change and there is a substantial rise in temperature of the vessel contents from room temperature, about 70 to 75 degrees F. (21-24 deg. C.), to 200 degrees F. (93 deg. C.) and there is evolution of smoke from the upper surface of the reaction liquor. The acid addition is made at such a slow rate as reach 180 deg. F. but to avoid boiling of the reaction liquor. After all the acid is added the final resulting reaction liquor or second solution is allowed to cool in air to room temperature. During this cooling the top surface of the second, reaction, liquor or solution exhibits a silky or glossy texture and thickens; there is no separating out of any component thereof and the resulting liquor is all in a single homogeneous liquid phase although of different, substantially darker, color than the initial orange color of the fish oil and the brownish color provided by the addition of the turpentine thereto. The cooled solution resulting from the reaction of the sulfuric acid with the turpentine and fish oil has a dark smooth black color.

During this reaction of concentrated sulfuric acid turpentine and fish oil the unsaturated olefinic portions in the components of the fish oil and the unsaturated ring compounds in the components of the turpentine, principally terpenes, react with the sulfuric acid and with each other, as shown by the rise in temperature and change in odor and color and viscosity of the reaction liquor. During this reaction of sulfuric acid and components of the turpentine and of fish oil the straight chain unsaturated compounds in the fish oil are condensed or cross-linked with the ring compounds of the turpentine. Such reaction provides substantially complete consumption of the sulfuric acid but is accomplished without destruction of the vitamin E content of the fish oil.

After the second or reaction liquor has cooled to room temperature (70-75 deg. F.) one ounce (29.6 ml) of oleic acid at room temperature is evenly and slowly added to the second reaction liquor with vigorous stirring. Such addition of oleic acid forms a resultant smooth and homogeneous third solution of slightly higher (3-5 deg. F.) temperature than the temperature of the second or reaction liquor to which added but no appreciable change in its color or change in its viscosity then occurs.

The oleic acid, in the quantity used thus dissolves in the second reaction liquor and forms a smooth (third) solution therewith but does not totally lose its drying or olefine characteristic. Because the oleic acid is added after the second or reaction liquor has cooled, it avoids decomposition so the unsaturated olefinic characteristic of the oleic acid for the most part are preserved although the oleic acid does act as a terminating agent for any sulfonation and condensation action that had earlier occurred or might later occur on storage. There is no free sulfuric acid present in the resultant third solution or composition after the completion of addition of oleic acid to second or reaction liquor.

To the third resultant solution or composition formed by the above described addition of oleic acid an ounce of purified kerosene is added. The kerosene is added slowly and with steady stirring to the third resultant solution or composition and forms a smooth homogeneous stable final solution or composition therewith. This kerosene has a low sulfur content (0.017% i.e. below 0.02 percent) and has a boiling range between 407 and 478 degrees F. (208–248 deg. C.). It consists essentially of paraffins, monocyclic and dicyclic napthenes, and some aromatic napthenes with 12 to 18 carbon atoms per molecule. The kerosene provides for penetration of the resulting final solution into fatty animal subcutaneous tissue but is low in sulfur to avoid irritation. The kerosene is hydrophobic and particularly provides for penetration of the composition into oleophilic material such as puss and provides a cleansing action thereon. The oleophilic quality of the third solution or composition into which the kerosene was added provides for stable suspension of such oleophilic material in contact with hydrophilic healthy animal tissue.

The final solution (after addition of the kerosene) is poured into one point polyethylene plastic bottles each of which is provided with a conventional hand pumped piston spray head dispenser at its top.

The resulting composition is applied to animal wounds by first washing the wound with water and then spraying the final composition onto the exposed wound. The final composition adheres to the exposed wound surface and forms a thin layer or skin thereover which, while flexible, protects the wound mechanically while, through the kerosene characteristics thereof, which is the most oleophilic and hydrophobic component of the final composition, provides for repelling of insects while the free oleic acid in the final composition prevents aerobic bacteria from contacting or growing in the tissue of the wound.

The relative amounts of turpentine and fish oil and acid are critical to provide selective bridging of like chemically potential active points and avoid excessive thickening and loss of fluidity; the oleic acid absorbs excess sulfuric acid as well as acting as an emollient while the unsaturated characteristic of the incompletely reacted fish oil and oleic acid prevent aerobic bacteria growth.

The overall or final composition thus produced penetrates dead tissues and selectively locates at the junction of healthy flesh in a wound and dead flesh and serves to protect the healthy flesh of the wound while causing the peripheral dead tissues to be sloughed off while also acting as an insect repellent and inhibiting bacterial growth so that the wound heals outwardly from the inner healthy tissue while the open wound is effectively shielded or covered by the overall or final composition.

In one case of application of the final composition produced the left jaw of a horse was punctured became sore and infected. While attempts by other medication only made the condition of the horse worse, after washing the sore with water and one application of the composition the sore noticeably improved in twelve hours and after two days with two applications daily of the final composition healing took over.

In another case of a deep cut on a horse the final composition was applied daily; it kept out proud flesh and healed nicely.

In another case a two year old gelding had developed an infection in his right foreleg. The final composition was applied as above described and the wound healed nicely in hot weather without developing proud flesh.

Other cases of a ripped fore leg and a horse's ankles have also been healed without development of proud flesh and without bother from flies, and no restraint or cradle was needed to protect the wounds while healing. One cut six inches wide and 10 inches long on a colt's throat was completely healed by application of the final composition of this invention as above described in six to eight weeks without development of proud flesh.

This fish oil above referred to also contains substantial amounts of vitamin A and vitamin D.

The fatty acids found in the fish oil above referred to and the approximate fatty acid compositions of the fish oil used in the above process and described compositions are set out in Table I below. In Table I column 1 is the range of percentage by weight of each acid; column 2 is the common name of each acid; the chemical name of each acid given in column 3 is in the Geneva system whereby the unsaturated bonds are indicated by counting from the carboxyl (COOH) carbon atom and the chemical name is given in column 4 in the simplified nomenclature of the biochemical system whereby the number of carbon atoms is listed followed by the number of unsaturated bonds and the position of the bond counting from the terminal methyl carbon atom or omega ($\omega$).

TABLE I

| Column 1 Percent Range | Column 2 Common Name | Column 3 Chemical Name Geneva system | Column 4 Simplified |
|---|---|---|---|
| 13–29 | Palmitic | Hexadecanoic acid | 16:0 |
| 4–13 | Plamitoleic | 9-Hexadecenoic acid | 16:1$\omega$7 |
| 9–22 | Oleic | 9-Octadecenoic acid | 18:1$\omega$9 |
| 1–3 | Linoleic | 9, 12-Octadecadienoic acid. | 18:2$\omega$6 |
| 2–3 | Linoleic | 6, 9, 12, 15-Octadecatetraenoic acid | 18:4$\omega$3 |
| 1–9 | Arachidic | 11-Eicosenoic acid | 20:1$\omega$9 |
| 1–3 | Arachidonic | 5, 8, 11, 14-Eicosotetraenoic acid | 20:4$\omega$6 |
| 9–12 | Arachidonic | 5, 8, 11, 14, 17-Eicosapentaenoic acid | 20:5$\omega$3 |
| 2–12 | Arachidonic | 13-Docosenoic acid | 22:1$\omega$9 |
| 1–3 | Arachidonic | 7, 10, 13, 16, 19-Docosahexaenoic acid | 22:5$\omega$3 |
| 8–13 | Arachidonic | 4, 7, 10, 13, 16, 19-Docosahexaenoic acid | 22:6$\omega$3 |
| 0–1 | Arachidonic | 15-Tetracosenoic acid | 24:1$\omega$9 |

I claim:

1. A process of forming an animal treating composition comprising the steps of:
   (a) mixing equal volumes of fish oil and turpentine to form a first combination composition and
   (b) adding 93–98% sulfuric acid to said first combination composition at a temperature of 180 degrees to 200 degrees F. said adding of sulfuric acid to said fish oil and turpentine composition being in the ratio of one fluid ounce of sulfuric acid to each portion of said first composition formed by one pint of fish oil and one pint of turpentine to form a second homogeneous composition, and thereafter cooling the second composition to room temperature.
   (c) adding oleic acid to said second composition to react with said second composition and thereby form a third homogeneous composition without free acid and wherein the amount of oleic acid added is one ounce thereof per portion of said first composition formed by one pint of fish oil and one pint of turpentine and wherein
   (d) purified kerosene in the amount of one ounce of kerosene per portion of said first composition formed by one pint of fish oil and one pint of turpentine, said kerosene having a boiling point of 208 to 248 degrees C. and a sulfur content below 0.02 percent, is added to and reacted with the third composition to form a fourth homogeneous solution.

2. Process of forming a therapeutic composition comprising the steps of
   (a) mixing equal volumes of
      (i) fish oil containing esters of long chain polyunsaturated acids, said chains comprising 20 to 24 carbon atoms and 1 to 6 olefinic bonds with
      (ii) turpentine containing terpenes chosen from the group comprising α pinene, β pinene, $\Delta^3$-carene, dipentene and terpinolene to form a first combination liquid composition, then
   (b) adding to said first combination composition 93–98% sulfuric acid in the ratio of one fluid ounce of sulfuric acid to each portion of said first composition formed by one pint of fish oil and one pint of turpentine and thereby causing a reaction at 180–200 degrees F. between said esters and said terpenes and forming a homogeneous second reaction liquor, then cooling said reaction liquor to room temperature, then
   (c) adding oleic acid to said cooled second reaction liquor and thereby forming a third resultant homogeneous solution and then
   (d) adding kerosene in the amount of one ounce of kerosene per portion of said first composition formed by one pint of fish oil and one pint of turpentine, and said kerosene having a boiling point of 208 to 248 degrees C. and a sulfur content below 0.02 percent, to said third resultant solution and reacting said kerosene with said third resultant solution to form a fourth homogeneous solution.

3. Process as in claim 2 wherein said esters are a glyceride.

4. Process as in claim 2 wherein the liquor containing said esters also comprises an antioxidant.

5. Process as in claim 4 wherein said antioxidant is alpha tocopherol.

6. An animal treating therapeutic composition formed by the process comprising the steps of:
   (a) mixing equal volumes of
      (i) fish oil containing esters of long chain polyunsaturated acids, said chains comprising 20 to 24 carbon atoms and 1 to 6 olefinic bonds, with
      (ii) turpentine containing terpenes chosen from the group comprising α pinene, β pinene, $\Delta^3$-carene, dipentene and terpinolene to form a first combination liquid composition, then
   (b) adding to said first combination composition 93–98% sulfuric acid in the ratio of one fluid ounce of sulfuric acid to each portion of said first composition formed by one pint of fish oil and one pint of turpentine and thereby causing a reaction at 180–200 degrees F. between said esters and said terpenes and forming a homogeneous second or reaction liquor, then cooling said reaction liquor to room temperature, then
   (c) adding oleic acid to said cooled reaction liquor and thereby forming a third resultant homogeneous solution and then
   (d) adding kerosene in the amount of one ounce of kerosene per portion of said first composition formed by one pint of fish oil and one pint of turpentine, said kerosene having a boiling point of 208 to 248 degrees C. and a sulfur content below 0.02 percent, to said third resultant solution and reacting it with said third resultant solution to form a fourth homogeneous solution.

7. Process of treating an open animal wound to prevent formation of proud flesh comprising the steps of washing the wound and thereafter applying an ointment made by the process of
   (i) mixing equal volumes of fish oil and turpentine to form a first combination composition and then
   (ii) adding 93–98% sulfuric acid to said first combination composition at a temperature of 180 degrees to 200 degrees F., said adding of sulfuric acid to the fish oil and turpentine being in the ratio of one fluid ounce of sulfuric acid to each portion of said first composition formed by one pint of fish oil and one pint of turpentine, to form a second homogeneous composition, and thereafter cooling said second composition to room temperature, and then
   (iii) adding oleic acid to said second composition to form a third homogeneous composition without free acid and wherein the amount of oleic acid added is one ounce per portion of said first composition formed by one pint of fish oil and one pint of turpentine and
   (iv) kerosene in the amount of one ounce of kerosene per portion of said first composition formed by one pint of fish oil and one pint of turpentine, said kerosene having a boiling point of 208 to 248 degrees C. and a sulfur content below 0.02 percent, is added to and reacted with the third composition to form a fourth homogeneous solution.

* * * * *